(12) United States Patent
Schmitt et al.

(10) Patent No.: US 6,171,608 B1
(45) Date of Patent: Jan. 9, 2001

(54) INSECTICIDE FORMULATIONS

(75) Inventors: Guido Schmitt; Gerd Schmitz; Klaus Walz, all of Leverkusen; Burkhard Mielke, Kürten; Hermann Neumann, Leverkusen, all of (DE)

(73) Assignee: Bayer Aktiengesellschaft, Leverkusen (DE)

( * ) Notice: Under 35 U.S.C. 154(b), the term of this patent shall be extended for 0 days.

(21) Appl. No.: 09/214,092

(22) PCT Filed: Jun. 19, 1997

(86) PCT No.: PCT/EP97/03199

§ 371 Date: Dec. 28, 1998

§ 102(e) Date: Dec. 28, 1998

(87) PCT Pub. No.: WO98/00020

PCT Pub. Date: Jan. 8, 1998

(30) Foreign Application Priority Data

Jul. 2, 1996 (DE) .............................................. 196 26 469

(51) Int. Cl.⁷ .......................... A01N 25/18; A01N 53/00; A01N 53/08
(52) U.S. Cl. ............................ 424/405; 424/40; 424/409; 514/531
(58) Field of Search ............................ 424/405, 40, 409; 514/531

(56) References Cited

U.S. PATENT DOCUMENTS

| 4,275,250 | 6/1981 | Naumann et al. . |
| 4,889,872 | 12/1989 | Naumann et al. . |
| 5,607,963 | * 3/1997 | Tsushima et al. ................... 514/425 |
| 5,645,845 | * 7/1997 | Neumann et al. ................... 424/405 |
| 5,707,638 | * 1/1998 | Losel et al. .......................... 424/407 |
| 5,965,602 | * 10/1999 | Takada et al. ....................... 514/427 |

FOREIGN PATENT DOCUMENTS

| 0 279 325 | 8/1988 | (EP) . |
| 2 379 506 | 9/1978 | (FR) . |
| 2 153 227 | 8/1985 | (GB) . |

OTHER PUBLICATIONS

Chemical Abstracts, vol. 126, No. 8, 1997 Columbus, Ohio, US; Katsuta: "Heat vaporizing aqueous insecticides containing . . .", XP002042231 (see abstract & JP 08 310 907 A).

Chemical Abstracts, vol. 126, No. 8 (1997), Abstract No. 100715, Katsuta: "Heat vaporizing aqueous insecticides . . . Conrol with them", (Abstract of JP 08 310 907).

* cited by examiner

Primary Examiner—Robert H. Harrison
(74) Attorney, Agent, or Firm—Norris, McLaughlin & Marcus, P.A.

(57) ABSTRACT

The present invention relates to novel liquid formulations for the controlled and sustained release of insecticidally active compounds by means of a heat source and the water-based pre-solutions required for preparing these formulations.

11 Claims, No Drawings

INSECTICIDE FORMULATIONS

The present invention relates to novel liquid formulations for the controlled and sustained release of insecticidally active compounds by means of a heat source and the pre-solutions required for preparing these formulations. The novel insecticidal formulations for the controlled and sustained release of insecticidally active compounds are characterized in that they comprise transfluthrin as insecticide and more than 90% of water as solvent.

Electrical heating devices, for example so-called tablet vaporizers, for killing insects, for example mosquitos, are known from the prior art. In this method, suitable materials, such as, for example, pulp and cotton cardboard, asbestos, ceramic and/or porous artificial resins are impregnated with insecticidally active compound solutions to obtain insecticide tablets. The insecticides are volatilized by the action of a heating device generating temperatures of 120–190° C.

A considerable disadvantage of these tablet vaporizers is the unfavorable ratio of energy input to amount of active compound to be vaporized, since the proportion of active compound in relation to the auxiliaries is low. Furthermore, owing to factors inherent in the system, i.e. the high operating temperature and the mode of action of these vaporizers, the active compounds are released in a very nonuniform manner over the prescribed duration of action. The duration of action of these vaporizer tablets is limited to a maximum of 12 hours. Finally, the unfavorable ratio of active compound to active compound carrier permanently requires a relatively large supply of vaporizer tablets, resulting in a considerable consumption of material.

Vaporizing devices for domestic use as described in GB 2 153 227, where the vaporization of an insecticidally active compound solution is effected by means of a heated wick and where the active compound is dissolved in a mixture of saturated aliphatic hydrocarbons which is vaporized electrically by using the wick, have been known for some time.

The amount of organic solvent required in these so-called liquid vaporizers, which is considerable in relation to the amount of active compound, results in a high indoor solvent concentration when the product is used.

This in turn causes walls and objects in the vicinity of these devices to become soiled, which is often complained about by users.

A decisive disadvantage of the formulations used in these devices is the fact that their use leads to permanently high concentrations of organic substances, such as saturated hydrocarbons, in the room air, which, for health reasons, is becoming less and less desirable.

A further disadvantage of these formulations is the risk of the flammable solvents leaking, leading to considerable problems during transport and storage and hazards during use.

The object of the present invention was to formulate insecticidally active compounds in such a way that they are not only storage-stable but can also, in addition to this, be vaporized undecomposed in combination with organic and inorganic auxiliaries, emulsifiers, solublilizers, stabilizers, antioxidants, perfumes and colorants from physiologically acceptable solutions in a uniform way and over a prolonged period by means of a heat source. The vaporization is to be carried out using a commercially available vaporizing device where a physiologically acceptable solution is absorbed by a suitable wick and released into the atmosphere by heating the upper part of this suitable wick.

The present invention thus relates to liquid formulations for vaporization using electric vaporizers fitted with a wick not having the disadvantages of the prior art owing to water being used as solvent. Since water is used as solvent, the formulations according to the invention are not flammable, and organochemical substances are released into the room air to a much lesser extent. This method for vaporizing an aqueous insecticidal solution can be employed for killing insects, such as, for example, mosquitos or moths.

In addition, the aqueous formulations according to the invention are simple to use in commercially available liquid vaporizers at the normal vaporizing temperatures of 100 to 160° C., and they ensure a continuous release of the active compound for up to 60 days, preferably up to 45 days.

The formulations according to the invention include formulations comprising insecticides, for example transfluthrin, water as solvent and one or more organochemical substances suitable as emulsifiers and/or co-surfactant. In addition, organic or inorganic auxiliaries, stabilizers, perfumes and/or colorants can be added to the mixtures.

The formulations according to the invention are prepared for example by initially preparing a pre-solution of transfluthrin, emulsifier and, if appropriate, co-surfactant which is then diluted to the desired emulsion volume by vigorous mixing with small portions of water. Further additives, perfumes and colorants can be admixed either to the pre-solution or to the ready-made-up diluted emulsion.

Alternatively, the formulations according to the invention can be obtained by directly mixing the individual components in succession.

The active compound transfluthrin is particularly suitable for the formulations according to the invention and applications thereof since it can be emulsified particularly well in the manner stated and in addition possesses the high thermal stability necessary for the application, so that, during vaporization, no decomposition products interfering with the transport process through the wick and the vaporization from the upper end of the wick are formed.

Other active compounds, such as, for example, d-allethrin or bioallethrin, which are conventionally used in liquid vaporizer systems have long been known to be poorly emulsifiable and to have the tendency to decompose when heated and to form decomposition products blocking the wick.

Suitable emulsifiers are, for example:

nonionic emulsifiers, such as reaction products of unsubstituted or substituted phenols, respectively optionally unsaturated or saturated fatty alcohols, fatty acids, fatty acid alkanolamides or fatty amines, vegetable oils or fats, partial fatty acid esters of polyols with ethylene oxide and, if appropriate, propylene oxide, sorbitan esters of fatty acids, fatty acid esters of polyols such as sucrose, glucose or sorbitan, anionic emulsifiers, such as respectively optionally saturated or unsaturated alkanesulfonates, alkyl sulfates, alkyl phosphates, alkyl ether sulfates, alkyl ether phosphates, salts of fatty acids, alkyl ether carboxylates, acyltaurides or acylsarcosides, each of which contains 8 to 22 carbon atoms, cationic emulsifiers, such as amine salts, quaternary ammonium compounds or imidazolinium compounds, each of which contains 8 to 22 carbon atoms, amphoteric emulsifiers, such as betaines, sulfobetaines or amine oxides, each of which contains 8 to 22 carbon atoms.

Preferred emulsifiers are:

reaction products of 4–50, in particular 8–30, mol of ethylene oxide and, if appropriate, propylene oxide with phenols (1 mol) substituted by one or more radicals ($C_1$–$C_{12}$)-alkyl, ($C_3$–$C_6$)-cycloalkyl-, phenyl-, phenyl-($C_1$–$C_3$)-alkyl-, or methylphenyl-($C_1$–$C_3$)-alkyl and reaction products of 5–50, in particular 8–30, mol (per equivalent of fatty radical) of ethylene oxide and, if appropriate, propylene oxide with ($C_{10}$–$C_{22}$)-fatty alcohols, fatty acids or fatty acid glycerides.

The aqueous formulations may additionally preferably also comprise alkali metal salts and/or alkaline earth metal salts of ($C_{10}$–$C_{20}$)-alkanesulfonic acids, in particular dodecylbenzenesulfonic acid, as further emulsifiers.

Particular preference is given to the following emulsifiers, which can be used on their own or in a mixture:

Emulsifier 1371 A (67% of alkylarylsulfonate, 23% of n-butanol, CAS # 90 194-26-6), a linear calcium arylsulfonate dissolved in n-butanol:

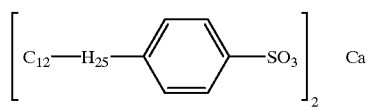

Emulsifier 1371 B (100% of fatty acid polyethylene glycol ether esters, CAS # 61791-12-6), a reaction product of castor oil with 20–40 mol of ethylene oxide, Emulsifier 368 pure (100% of aryl polyglycol ether, CAS # 73297-33-3) of the following formula:

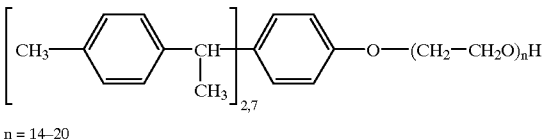

n = 14–20

Emulsifier PS 16 (100% of aryl polyglycol ether, CAS # 104376-75-2) of the following formula:

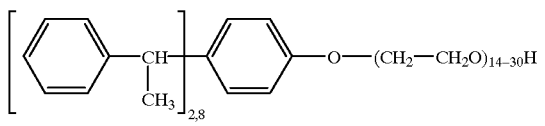

Emulsifier PS 29 (100% of aryl polyglycol ether, CAS # 104376-75-2) of the following formula:

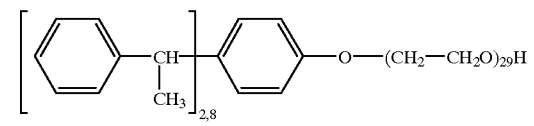

Emulsifier L7 (100 of fatty alcohol polyglycol ether, CAS # 68213-23-0) of the following formula:
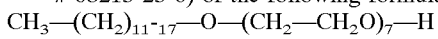

Reaction products of optionally unsaturated fatty alcohols, containing 12–18 carbon atoms, with 6–15, in particular 7–10, mol of ethylene oxide,
if appropriate in combination with alkali metal salts and/or alkaline earth metal salts of ($C_{10}$—$C_{20}$)-alkanesulfonic acids, in particular dodecylbenzenesulfonic acid.

Examples of co-surfactants include:
straight-chain or branched alcohols having 3 to 10 carbon atoms, cycloalkanols having 5 to 8 carbon atoms, ($C_2$—$C_6$)-alkyl esters of ($C_2$—$C_6$)-hydroxycarboxylic acids, ($C_1$—$C_{12}$)-alkylpyrrolidones, ($C_1$—$C_{12}$)-alkylcaprolactams, cyclohexylpyrrolidone or cyclohexylcaprolactam, N,N-dimethyl- or N,N-diethyl-($C_4$—$C_{12}$)-carboxamides, benzyl alcohol and high boiling mineral oils.

Preferred co-surfactants are:
aliphatic ($C_3$—$C_8$)-alcohols, cyclohexanol, methylcyclohexanol, ($C_3$—$C_4$)-alkyl lactates, cyclohexylpyrrolidone, octylpyrrolidone, decylpyrrolidone, dodecylpyrrolidone, dimethylamides of octanoic acid, decanoic acid and undecanoic acid, or high boiling mineral oils.

It is possible to add colorants to the formulations according to the invention, for example:
inorganic pigments, for example iron oxide, titanium oxide and Prussian Blue,
organic dyestuffs, such as alizarin, azo dyestuffs and metal phthalocyanine dyestuffs,
and trace nutrients such as salts of iron, manganese, boron, copper, cobalt, molybdenum and zinc.

These additions of colorants to the formulations according to the invention facilitate the identification of the liquid in the storage container and can also be used for visual identification of the end point of the biological effectiveness of the system.

A variant of the visual end point identification using added colorants may also take the form of a change in color when the active compounds and water have evaporated.

Deodorants, such as, for example, lauryl methacrylate, geranyl crotonate, acetophenone myristate, p-methylacetophenone benzaldehyde, benzyl acetate, benzyl propionate, amyl cinnamaldehyde, anisaldehyde, diphenyl oxide, methyl benzoate, ethyl benzoate, methylphenyl acetate, ethylphenyl acetate, neoline, safrole, and the like, may be added to the formulations according to the invention.

Other substances which can furthermore be added to the formulations according to the invention are natural perfumes such as, for example, musk, civet, ambergris, castoreum and similar perfumes; ajowa oil, almond oil, absolute of amberseed, angelica root oil, aniseed oil, basil oil, bay oil, benzoin resinoid, essence of bergamot, birch oil, rosewood oil, absolute of common broom, cajeput oil, cananga oil, capsicum oil, caraway oil, cardamom oil, carrot seed oil, cassia oil, cedar wood oil, celery seed oil, cinnamon bark oil, citronella oil, clary sage oil, clove oil, cognac oil, coriander oil, cubeb oil, camphor oil, dill oil, taragon oil, eucalyptus oil, sweet fennel oil, galbanum resinoid, garlic oil, geranium oil, ginger oil, grapefruit oil, hop oil, absolute of hyacinth, absolute of jasmine, juniper berry oil, labdanum resinoid, lavender oil, bay leaf oil, lemon oil, lemon grass oil, lovage oil, mace oil, mandarin oil, absolute of mimosa, absolute of myrrh, mustard oil, absolute of narcissus, neroli -oil, nutmeg oil, absolute of oak moss, olibanum resinoid, onion oil, opoponax resinoid, orange oil, orange flower oil, concrete iris, pepper oil, peppermint oil, Perubalsam, petitgrain oil, pine needle oil, absolute of rose, rose oil, rosemary oil, sandalwood oil, sage oil, spearmint oil, storax oil, thyme oil, balsam of tolu, absolute of tonka bean, absolute of tuberose, turpentine oil, absolute of vanilla pod, vetiver oil, absolute of violet leaves, ylang-ylang oil and similar vegetable oils and the like.

Synthetic perfumes which can be added to the formulations according to the invention are:
pinene, limonene and similar hydrocarbons; 3,3,5-trimethylcyclohexanol, linalool, geraniol, nerol, citronellol, menthol, borneol, borneylmethoxycyclohexanol, benzyl alcohol, anisyl alcohol, cinnamyl alcohol, phenylethyl alcohol, cis-3-hexanol, terpineol and similar alcohols; anetholes, musk xylene, isoeugenol, methyleugenol and similar phenols; amylcinnamaldehyde, anisaldehyde, n-butyraldehyde, cuminaldehyde, cydlamenaldehyde, decyl aldehyde, isobutyraldehyde, hexaldehyde, heptaldehyde, n-nonyl aldehyde nonadienol, citral, citronellal, hydroxycitronellal, benzaldehyde, methyl-nonyl acetaldehyde, cinnamaldehyde, dodecanol, hexylcinnamaldehyde, undecanal, heliotropin, vanillin, ethylvanillin, and similar aldehydes, methyl amyl ketone, methyl naphthyl ketone, methyl nonyl ketone, musk ketone, diacetyl, acetylpropionyl, acetylbutyryl, carvone, methone, camphor, acetophenone, p-methylacetophenone, ionone, methylionone and similar ketones; amyl-butyrolactone, diphenyl oxide, methylphenyl glycidate, nonylacetone, coumarin, cineol, ethylmethylphenyl glycidate and similar lactones or oxides, methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl caproate, butyl heptylate, octyl caprylate, methyl heptinecarboxylate, methyl octinecarboxylate, isoamyl caprylate, methyl laurate, ethyl myristate, methyl myristate, ethyl benzoate, benzyl benzoate, methylcarbinylphenyl acetate, isobutylphenyl acetate, methyl cinnamate, styracin, methyl salicylate, ethyl anisate, methyl anthranilate, ethyl pyruvate, ethyl butylbutyrate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethylphenyl acetate, ethylene brassylate, geranyl acetate, geranyl formate, isoamyl salicylate, isoamyl valerate, isobornyl acetate, linolyl acetate, methyl anthranilate, methyl dihydrojasmonate, nonyl acetate, phenylethyl acetate, trichloromethylenephenylcarbinyl acetate, terpinyl acetate, vetiveryl acetate and similar esters.

These perfumes can be used on their own, or it is possible to use at least two thereof as a mixture with each other. In addition to perfume, the formulation according to the invention can, if appropriate, additionally comprise the additives conventionally used in the perfume industry, such as patchouli oil or similar volatilization inhibitors, such as eugenol, or similar viscosity regulators.

The formulations according to the invention generally comprise between 0.01 and 95% by weight of transfluthrin, preferably between 0.1 and 10% by weight.

The formulations according to the invention further comprise between 0.01 and 20% by weight, preferably between 0.01 and 5% by weight, of emulsifier and, if appropriate, between 0.01 and 20% by weight, preferably between 0.01 and 5% by weight, of one or more co-surfactant.

The pre-solutions used in the preparation generally comprise between 10 and 70% by weight of transfluthrin, preferably between 15 and 40% by weight.

The pre-solutions further comprise between 10 and 70% by weight, preferably between 15 and 40% by weight, of emulsifier and, if appropriate, between 10 and 60% by weight, preferably between 20 and 45% by weight, of co-surfactant.

The preparation, compositions and the properties of the novel insecticidal formulations according to the invention are illustrated by the examples below.

EXAMPLE 1

Preparation of the pre-solutions

The emulsifier and the active compound are initially charged and homogenized by stirring at room temperature for 10 minutes. After the homogenization, the co-surfactant and, if appropriate, water are slowly added with stirring at room temperature.

In this manner, the pre-solutions below were prepared:

| Example No. | Component | Percentage |
|---|---|---|
| 1.1. | Transfluthrin | 43.0% |
| | N-Octylpyrrolidone | 40.0% |
| | Emulsifier 368 pure | 8.5% |
| | Emulsifier PS 29 | 8.5% |
| 1.2. | Transfluthrin | 45.0% |
| | N-Octylpyrrolidone | 40.0% |
| | Emulsifier 368 pure | 7.5% |
| | Emulsifier PS 29 | 7.5% |
| 1.3. | Transfluthrin | 26.6% |
| | N-Octylpyrrolidone | 25.0% |
| | Emulsifier 368 pure | 10.0% |
| | Isopropanol | 1.0% |
| | Water | 37.4% |
| 1.4. | Transfluthrin | 40.0% |
| | Emulsifier 368 pure | 30.0% |
| | 1-Butanol | 10.0% |
| | Water | 20.0% |
| 1.5. | Transfluthrin | 30.0% |
| | Emulsifier 368 pure | 40.0% |
| | 1-Butanol | 30.0% |
| 1.6. | Transfluthrin | 40.0% |
| | Marlowet OFA* | 20.0% |
| | Isopropanol | 20.0% |
| 1.7. | Transfluthrin | 40.0% |
| | Emulsifier 368 pure | 40.0% |
| | Isopropanol | 20.0% |
| 1.8. | Transfluthrin | 40.0% |
| | Emulsifier 1371 B | 26.7% |
| | Isopropanol | 33.3% |
| 1.9. | Transfluthrin | 40.0% |
| | Emulsifier 1371 B | 40.0% |
| | Isopropanol | 20.0% |
| 1.10. | Transfluthrin | 19.40% |
| | Emulsifier L7 | 3.70% |
| | Emulsifier 368 | 7.30% |
| | Na ABS solution (10%) | 2.20% |
| | Isopropanol | 0.80% |
| | N-Octylpyrrolidone | 22.60% |
| | Water | 44.0% |
| 1.11. | Transfluthrin | 20.0% |
| | Emulsifier L7 | 4.50% |
| | Emulsifier 368 | 9.00% |
| | Na ABS solution (10%) | 4.50% |
| | Isopar V | 20.00% |
| | N-Octylpyrrolidone | 23.00% |
| | Water | 19.00% |
| 1.12. | Transfluthrin | 30.00% |
| | Emulsifier 1371 A | 10.00% |
| | Emulsifier L7 | 15.00% |
| | Isopar V | 40.00% |
| | Water | 5.0% |
| 1.13. | Transfluthrin | 17.00% |
| | Emulsifier 1371 A | 10.00% |
| | Emulsifier L7 | 15.00% |
| | Isopar V | 51.00% |
| | Water | 7.0% |

*Marlowet OFA is a surfactant mixture comprising:
triethanolamine salts of $C_{10}$–$C_{13}$-alkylbenzenesulfonic acid
ethoxylated oleic acid
triethanolamine and
ethoxylated dodecanol

EXAMPLE 2

Preparation of the insecticidal vaporizer solutions

The pre-solution is initially charged. The calculated amount of demineralized water is added in small portions with vigorous mixing, forming an opalescent emulsion.

In this manner, the following solutions were prepared:

| Example No. | Component | Percentage |
| --- | --- | --- |
| 2.1. | Transfluthrin | 1.00% |
| | N-Octylpyrrolidone | 0.93% |
| | Emulsifier 368 pure | 0.20% |
| | Emulsifier PS 29 | 0.20% |
| | Water | 97.67% |
| 2.2. | Transfluthrin | 1.00% |
| | N-Octylpyrrolidone | 0.89% |
| | Emulsifier 368 pure | 0.19% |
| | Emulsifier PS 29 | 0.19% |
| | Water | 97.73% |
| 2.3. | Transfluthrin | 0.40% |
| | Emulsifier 1371 B | 0.20% |
| | Isopropanol | 0.50% |
| | Water | 98.90% |
| 2.4. | Transfluthrin | 0.40% |
| | Emulsifier 1371 B | 0.30% |
| | Isopropanol | 0.50% |
| | Water | 98.80% |
| 2.5. | Transfluthrin | 0.40% |
| | Emulsifier 1371 B | 0.40% |
| | Isopropanol | 0.50% |
| | Water | 98.70% |
| 2.6. | Transfluthrin | 0.80% |
| | Emulsifier 1371 B | 0.60% |
| | Isopropanol | 0.50% |
| | Water | 98.10% |
| 2.7. | Transfluthrin | 0.40% |
| | Emulsifier 1371 B | 0.20% |
| | Isopropanol | 0.50% |
| | Water | 98.90% |
| 2.8. | Transfluthrin | 0.80% |
| | Emulsifier 1371 B | 0.70% |
| | Isopropanol | 0.50% |
| | Water | 98.00% |
| 2.9. | Transfluthrin | 0.80% |
| | Emulsifier 1371 B | 0.80% |
| | Isopropanol | 0.50% |
| | Water | 97.90% |
| 2.10. | Transfluthrin | 1.00% |
| | Emulsifier 1371 B | 0.50% |
| | Isopropanol | 0.50% |
| | Water | 98.00% |
| 2.11. | Transfluthrin | 1.00% |
| | Emulsifier 1371 B | 0.60% |
| | Isopropanol | 0.50% |
| | Water | 97.90% |
| 2.12. | Transfluthrin | 1.00% |
| | Emulsifier 1371 B | 0.70% |
| | Isopropanol | 0.50% |
| | Water | 97.80% |
| 2.13. | Transfluthrin | 1.00% |
| | Emulsifier 1371 B | 0.80% |
| | Isopropanol | 0.50% |
| | Water | 97.70% |
| 2.14. | Transfluthrin | 1.00% |
| | Emulsifier 1371 B | 0.90% |
| | Isopropanol | 0.50% |
| | Water | 97.60% |
| 2.15. | Transfluthrin | 1.00% |
| | Emulsifier 1371 B | 1.00% |
| | Isopropanol | 0.50% |
| | Water | 97.50% |
| 2.16 | Transfluthrin | 1.00% |
| | Emulsifier 368 pure | 0.34% |
| | N-Octylpyrrolidone | 0.94% |
| | Isopropanol | 0.04% |
| | Water | 97.68% |
| 2.17. | Transfluthrin | 1.00% |
| | Emulsifier 1371 B | 1.32% |
| | 1-Butanol | 0.33% |
| | Water | 97.35% |
| 2.18. | Transfluthrin | 0.80% |
| | Emulsifier 1371 B | 0.80% |
| | Isopropanol | 0.40% |
| | Water | 98.00% |
| 2.19. | Transfluthrin | 1.00% |
| | Emulsifier 1371 B | 0.67% |
| | Isopropanol | 0.83% |
| | Water | 97.50% |
| 2.20. | Transfluthrin | 0.70% |
| | Emulsifier 1371 B | 1.00% |
| | Benzyl alcohol | 4.00% |
| | Isopropanol | 25.00% |
| | Butylhydroxytoluene | 1.00% |
| | Water | 68.30% |
| 2.21. | Transfluthrin | 0.50% |
| | Butylhydroxytoluene | 1.00% |
| | Diethylene glycol monobutyl ether | 52.50% |
| | Water | 46.00% |
| 2.22. | Transfluthrin | 0.70% |
| | Butylhydroxytoluene | 1.00% |
| | Diethylene glycol monobutyl ether | 58.30% |
| | Water | 40.00% |
| 2.23. | Transfluthrin | 1.50% |
| | Butylhydroxytoluene | 1.00% |
| | Diethylene glycol monobutyl ether | 51.50% |
| | Water | 46.00% |
| 2.24. | Transfluthrin | 0.80% |
| | Emulsifier L7 | 0.15% |
| | Emulsifier 368 | 0.30% |
| | Na ABS solution (10%) | 0.09% |
| | Isopropanol | 0.03% |
| | N-octylpyrrolidone | 0.93% |
| | Water | 97.70% |
| 2.25. | Transfluthrin | 0.80% |
| | Emulsifier L7 | 0.18% |
| | Emulsifier 368 | 0.36% |
| | Na ABS solution (10%) | 0.18% |
| | Isopar V | 0.80% |
| | N-Octylpyrrolidone | 0.92% |
| | Water | 96.76% |
| 2.26. | Transfluthrin | 0.80% |
| | Emulsifier 1371 A | 0.27% |
| | Emulsifier L7 | 0.40% |
| | Isopar V | 1.07% |
| | Water | 97.46% |
| 2.27 | Transfluthrin | 0.82% |
| | Emulsifier 1371 A | 0.49% |
| | Emulsifier L7 | 0.73% |
| | Isopar V | 2.47% |
| | Water | 95.49% |

EXAMPLE 3

Release characteristics of the insecticidal vaporizer solutions according to the invention Examples 3.1 to 3.3 show the evaporation characteristics of an exemplary insecticidal formulation according to the invention using various wick systems. The evaporation rates are shown in mg/h and the cumulative amounts evaporated are stated in percent.

Example 3.1 Formulation 2.15

Wick: f-32138 acetate fibers/perforated - coating
Bottle: PET
Heater: Standard KS Test Conditions:
Temperature: 130° C.
Duration of cycle: 8h
Cycle sequence: 8/4/8/4

Active compound: Transfluthrin

| Heater: | 1 | 2 | 3 | 4 | 5 |
|---|---|---|---|---|---|
| | 130° C. | 130° C. | 130° C. | 130° C. | 130° C. |

Formulation 2.15
Transfluthrin 1.00%
Isopropanol 0.50%
Emul. 1371 B 1.00%
Demin. water 97.50%

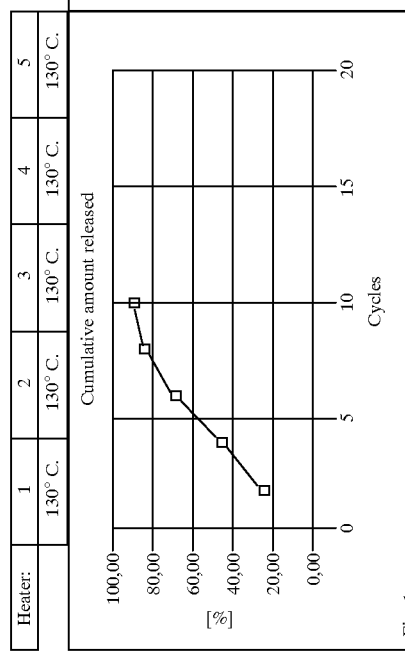

Fig. 1

Cumulative amount release of the active compound emulsion in [%] against the cycle sequence (1 cycle = 8 h of use) for the formulation 2.15 using the transport wick f-32138 acetate fibers/perforated - coating

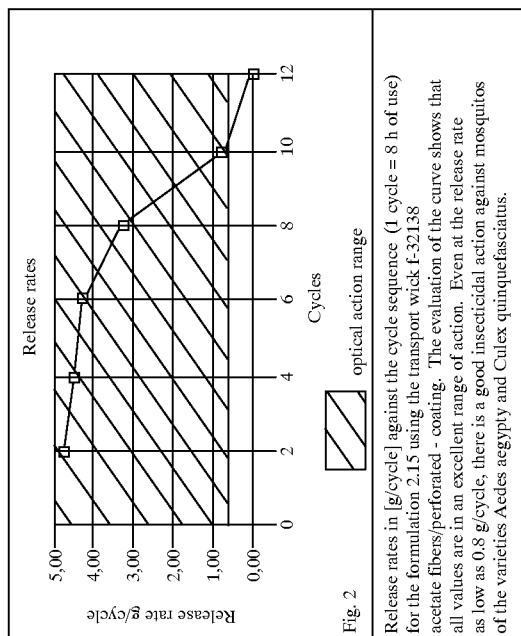

Fig. 2

Release rates in [g/cycle] against the cycle sequence (1 cycle = 8 h of use) for the formulation 2.15 using the transport wick f-32138 acetate fibers/perforated - coating. The evaluation of the curve shows that all values are in an excellent range of action. Even at the release rate as low as 0.8 g/cycle, there is a good insecticidal action against mosquitos of the varieties Aedes aegypty and Culex quinquefasciatus.

Example 3.2 Formulation 2.15

Wick: f-16566 PE fibers
Bottle: PET

Heater: Standard KS

Test Conditions:
Temperature: 130° C.
Duration of cycle: 8h
Cycle sequence: 8/4/8/4

Active compound: Transfluthrin

| Heater: | 1 | 2 | 3 | 4 | 5 |
|---|---|---|---|---|---|
| | 130° C. | 130° C. | 130° C. | 130° C. | 130° C. |

Formulation 2.15
Transfluthrin 1.00%
Isopropanol 0.50%
Emul. 1371 B 1.00%
Demin. water 97.50%

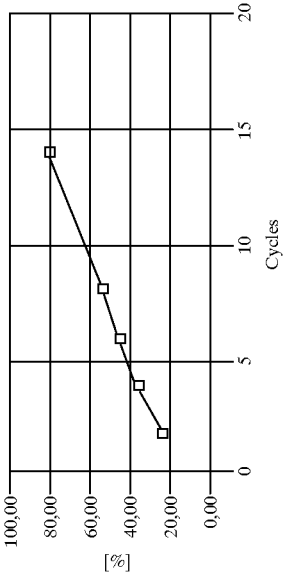

Fig. 3

Cumulative amount release of the active compound emulsion in [%] against the cycle sequence (1 cycle = 8 h of use) for the formulation 2.15 using the transport wick f-16566 PE fibers

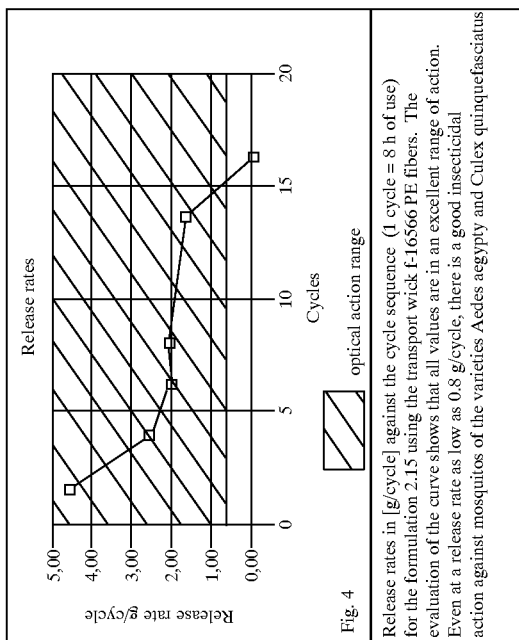

Fig. 4

Release rates in [g/cycle] against the cycle sequence (1 cycle = 8 h of use) for the formulation 2.15 using the transport wick f-16566 PE fibers. The evaluation of the curve shows that all values are in an excellent range of action. Even at a release rate as low as 0.8 g/cycle, there is a good insecticidal action against mosquitos of the varieties Aedes aegypty and Culex quinquefasciatus Example 3.3 Formulation 2.15

Wick: Ceramic 60%
Bottle: PET

Heater: Standard KS

Test Conditions:
Temperature: 130° C.
Duration of cycle: 8h
Cycle sequence: 8/4/8/4

Active compound: Transfluthrin

| Heater: | 1 | 2 | 3 | 4 | 5 |
|---|---|---|---|---|---|
| | 130° C. | 130° C. | 130° C. | 130° C. | 130° C. |

Formulation 2.15
Transfluthrin 1.00%
Isopropanol 0.50%
Emul. 1371 B 1.00%
Demin. water 97.50%

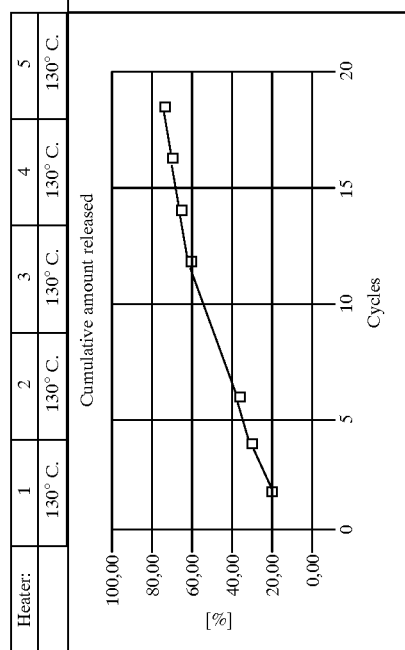

Fig. 5

Cumulative amount release of the active compound emulsion in [%] against the cycle sequence (1 cycle = 8 h of use) for the formulation 2.15 using the transport wick 60%

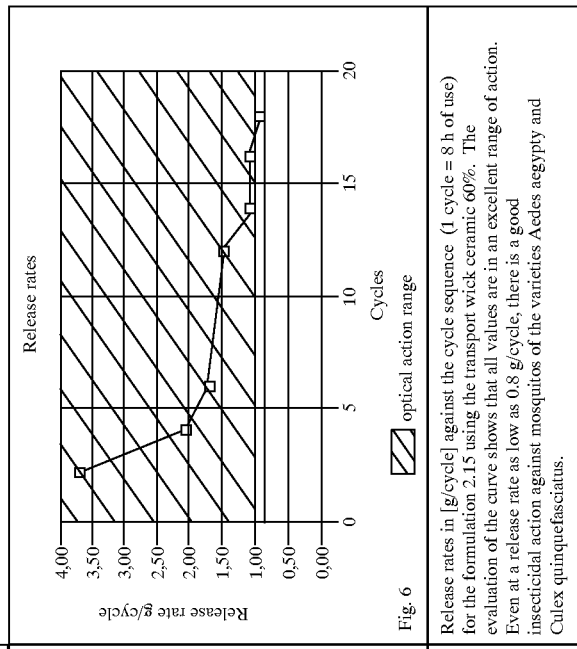

Fig. 6

Release rates in [g/cycle] against the cycle sequence (1 cycle = 8 h of use) for the formulation 2.15 using the transport wick ceramic 60%. The evaluation of the curve shows that all values are in an excellent range of action. Even at a release rate as low as 0.8 g/cycle, there is a good insecticidal action against mosquitos of the varieties Aedes aegypty and Culex quinquefasciatus.

What is claimed is:

1. An insecticidal formulation comprising:
   a) transfluthrin;
   b) one or more emulsifiers;
   c) one or more co-surfactants selected from the group consisting of straight-chain or branched alcohols having 3 to 10 carbon atoms, cycloalkanols having 5 to 8 carbon atoms, $C_2$—$C_6$-alkyl esters of $C_2$—$C_6$-hydroxy-carboxylic acids, $C_1$—$C_{12}$-alkylpyrrolidones, $C_1$—$C_{12}$-alkylcaprolactams, cyclohexylpyrrolidone or cyclohexylcaprolactam, N,N-dimethyl- or N,N-diethyl-($C_4$—$C_{12}$)-carboxamides, benzyl alcohol and high boiling mineral oils; and
   d) water.

2. The insecticidal formulation according to claim 1, which comprises at least one of organic or inorganic auxiliaries, stabilizers, perfumes and colorants.

3. The insecticidal formulation according to claim 1, which comprises one or more emulsifiers independently selected from the group consisting of nonionic emulsifiers, anionic emulsifiers, cationic emulsifiers and amphoteric emulsifiers.

4. The insecticidal formulation according to claim 3, wherein the nonionic emulsifiers are selected from the group consisting of reaction products of unsubstituted or substituted phenols, optionally unsaturated or saturated fatty alcohols, fatty acids, fatty acid alkanolamides or fatty amines, vegetable oils or fats, partial fatty acid esters of polyols with ethylene oxide and, optionally, propylene oxide, sorbitan esters of fatty acids, and fatty acid esters of polyols; the anionic emulsifiers are selected from the group consisting of optionally saturated or unsaturated alkanesulfonates, alkyl sulfates, alkyl phosphates, alkyl ether sulfates, alkyl ether phosphates, salts of fatty acids, alkyl ether carboxylates, acyltaurides and acylsarcosides, each of which contains 8 to 22 carbon atoms; the cationic emulsifiers are selected from the group consisting of amine salts, quaternary ammonium compounds and imidazolinium compounds, each of which contains 8 to 22 carbon atoms; and the amphoteric emulsifiers are selected from the group consisting of betaines, sulfobetaines and amine oxides, each of which contains 8 to 22 carbon atoms.

5. The insecticidal formulation according to claim 1, which comprises at least one emulsifier which is a reaction product of 4–50 mol of ethylene oxide and optionally propylene oxide with phenols (1 mol) which are substituted by one or more radicals of ($C_1$—$C_{12}$)-alkyl, ($C_3$—$C_6$)-cycloalkyl-, phenyl-, phenyl ($C_1$—$C_3$)-alkyl-, and/or methylphenyl-($C_1$—$C_3$)-alkyl and/or a reaction product of 5–50 mol (per equivalent of fatty acid radical) ethylene oxide and optionally propylene oxide with ($C_{10}$—$C_{22}$)-fatty alcohols, fatty acids or fatty acid glycerides.

6. The insecticidal formulation according to claim 1, which comprises at least one of colorants, deodorizing agents and natural or synthetic perfumes.

7. The insecticidal formulation according to claim 1, which comprises 0.01 to 95% by weight of transfluthrin based on the total weight of the formulation.

8. The insecticidal formulation according to claim 4, which comprises 0.01 to 20% by weight of emulsifier based on the total weight of the formulation.

9. The insecticidal formulation according to claim 1, which comprises more than 90% by weight of water based on the total weight of the formulation.

10. A process for preparing an insecticidal formulation according to claim 1, said process comprising preparing a pre-solution comprising said transfluthrin, said one or more emulsifiers and said co-surfactants, and then diluting said pre-solution to a desired formulation volume by vigorous mixing of said pre-solution with small portions or water.

11. A pre-solution for preparing an insecticidal formulation according to claim 1, said pre-solution comprising:
   a) 10–70% by weight of transfluthrin;
   b) 10–70% by weight of total emulsifier; and
   c) 10–60% by weight of total co-surfactant, wherein the total co-surfactant consists of one or more co-surfactants selected from the group consisting of straight-chain or branched alcohols having 3 to 10 carbon atoms, cycloalkanols having 5 to 8 carbon atoms, $C_2$—$C_6$-alkyl esters of $C_2$—$C_6$-hydroxy-carboxylic acids, $C_1$—$C_{12}$-alkylpyrrolidones, $C_1$—$C_{12}$-alkylcaprolactams, cyclohexylpyrrolidone or cyclohexylcaprolactam, N,N-dimethyl- or N,N-diethyl-($C_4$—$C_{12}$)-carboxamides, benzyl alcohol and high boiling mineral oils.

* * * * *